(12) United States Patent
Kamada (10) Patent No.: US 8,431,548 B2
(45) Date of Patent: Apr. 30, 2013

(54) METHOD FOR PLACENTAL EXFOLIATION USING OXO-ARACHIDONIC ACID OR THE LIKE

(75) Inventor: Hachiro Kamada, Ibaraki (JP)

(73) Assignee: Incorporated Administrative Agency National Agriculture and Food Research Organization, Tsukuba-shi (JP)

( * ) Notice: Subject to any disclaimer, the term of this patent is extended or adjusted under 35 U.S.C. 154(b) by 0 days.

(21) Appl. No.: 13/219,364

(22) Filed: Aug. 26, 2011

(65) Prior Publication Data

US 2012/0010289 A1  Jan. 12, 2012

Related U.S. Application Data

(62) Division of application No. 12/104,260, filed on Apr. 16, 2008, now Pat. No. 8,034,841.

(30) Foreign Application Priority Data

Sep. 21, 2007  (JP) ................................. 2007-246032

(51) Int. Cl.
*A01N 37/00* (2006.01)
*A61K 31/20* (2006.01)

(52) U.S. Cl.
USPC ......................................................... 514/56

(58) Field of Classification Search .................. None
See application file for complete search history.

(56) References Cited

U.S. PATENT DOCUMENTS 5,508,307 A  4/1996  Horrobin et al.

FOREIGN PATENT DOCUMENTS

JP  6-157304 A  6/1994

OTHER PUBLICATIONS

Office Action issued Oct. 2, 2012 in Japanese Patent Application No. 2007-246032.
Hachiro Kamada, et al., "Influence of various inhibitors on activity of arachidonic acid for exfoliating placenta-derived fibroblasts", Hokkaido Agricultural Research Center, National Agriculture and Bio-Oriented Research Organization, vol. $104^{th}$, 2005, p. 117 (with English translation).
Bernard Fruteau de Laclos, et al., "Conditions for the formation of the oxo derivatives of arachidonic acid from platelet 12-lipoxygenase and soybean 15-lipoxygenase", Biochimica et Biophysica Acta, vol. 958, No. 3, 1988, pp. 424-433.
Nakahara, et al. "Induction of Parturition in Cattle with Prostaglandin $F_{2\alpha}$"Jap. J. Aninal Reprod. vol. 21, No. 4, pp. 135-140 (1976).
Kamimura, et al. "Induction of Abortion and Parturition with Corticosteroids in Dairy Cattle", Japan. J. Anim. Reprod. vol. 23, No. 3, pp. 85-92 (1977).
Kouzou, et al., "The Timed Induction of Parturition by Simultaneous Injection of Prostaglandi $F_{2\alpha}$, and Dexamethasone in Japanese Black Beef Cows", J. Livestock Med, vol. 52, No. 11, pp. 673-681 (2005).
Hugo, et al., "Successful Treatment of Retained Placenta with Umbilical Cord Injections of Collagenase in Cows", JAVMA, vol. 203, No. 3, pp. 436-443, Aug. 1, 1993.
J. G. Maj, et al. "Activity of 72-kDa and 92-kDa Matrix Metalloproteinases in Placental Tissues of Cows With and Without Retained Fetal Membranes", Placenta, vol. 18 pp. 683-687, 1997.
Slama et al (Prostaglandins 45:57-75, 1993; Abstract only).
Stocker et al, (Veterinary Record 132:507-508, 1993; Abstract only).
Prior-Curtin (The Eicosanoids, p. 61, 2004).

*Primary Examiner* — Craig Ricci
(74) *Attorney, Agent, or Firm* — Oblon, Spivak, McClelland, Maier & Neustadt, L.L.P.

(57) ABSTRACT

A composition for placental exfoliation and a method for placental exfoliation. The composition for placental exfoliation contains an arachidonic acid derivative or the like, and the method for placental exfoliation comprises the step of administering an arachidonic acid derivative or the like to a mammal after the fetal delivery.

8 Claims, 5 Drawing Sheets

METHOD FOR PLACENTAL EXFOLIATION USING OXO-ARACHIDONIC ACID OR THE LIKE

BACKGROUND OF THE INVENTION

1. Field of the Invention

The present invention relates to methods for placental exfoliation and methods for parturition induction, for example.

2. Background Art

The livestock industry related to farm animals such as cattle is said to be profitable provided with the successful reproduction. However, in the case of Hokkaido Japan, the economic loss caused by the deterioration in the reproductive performance has been preliminarily calculated as 3 million yen or more per dairyman on average. As one of the causative factors of this deterioration in the reproductive performance, technical inadequacies and accidents related to the parturition can be enumerated. These technical inadequacies and accidents related to the parturition lead to the increase in the mortality rate of newborns and the lowering in the success rate of conception. Moreover, overworks involved in the attendance in the midnight parturition are also raising big problems at the production site of the livestock industry where aging of stock raising farmers is in progress.

Under such situations, the parturition-related techniques required by stock raising farmers include techniques for safely inducing the daytime parturition so as to avoid the attendance in the midnight parturition, and parturition induction techniques for preventing the placental retention so as to avoid a difficult delivery caused by an oversized fetus beyond the due date. These techniques bring up various effects such as reduced incidence of accident during the parturition, alleviation of mental and physical strain on the manager, appropriate management of the newborn (supply of colostrum without delay), and normal recovery of a maternal farm animal after parturition.

Examples of the above parturition-related techniques which are conventionally performed include, in cases of cows, the induction of daytime parturition by limiting the feeding time and the parturition induction using hormones (glucocorticoid or prostaglandin).

The induction of daytime parturition by limiting the feeding time is specifically performed by feeding during the night time, removing the leftover in the morning, and giving no food during the day time (Wolfe, Modern veterinary practice, Vol. 64, p. 21-23 (1983); and Aoki et al., Animal Science Journal, Vol. 77, No. 3, p. 290-299 (2006)). However, the concerned induction yields about 70% probability of the daytime parturition. Moreover, it is unknown when the parturition after the treatment occurs. Furthermore, this technique can not be used for cows suffering from prolonged gestation when calving would not occur even after a long-delayed due date.

Figure 1:
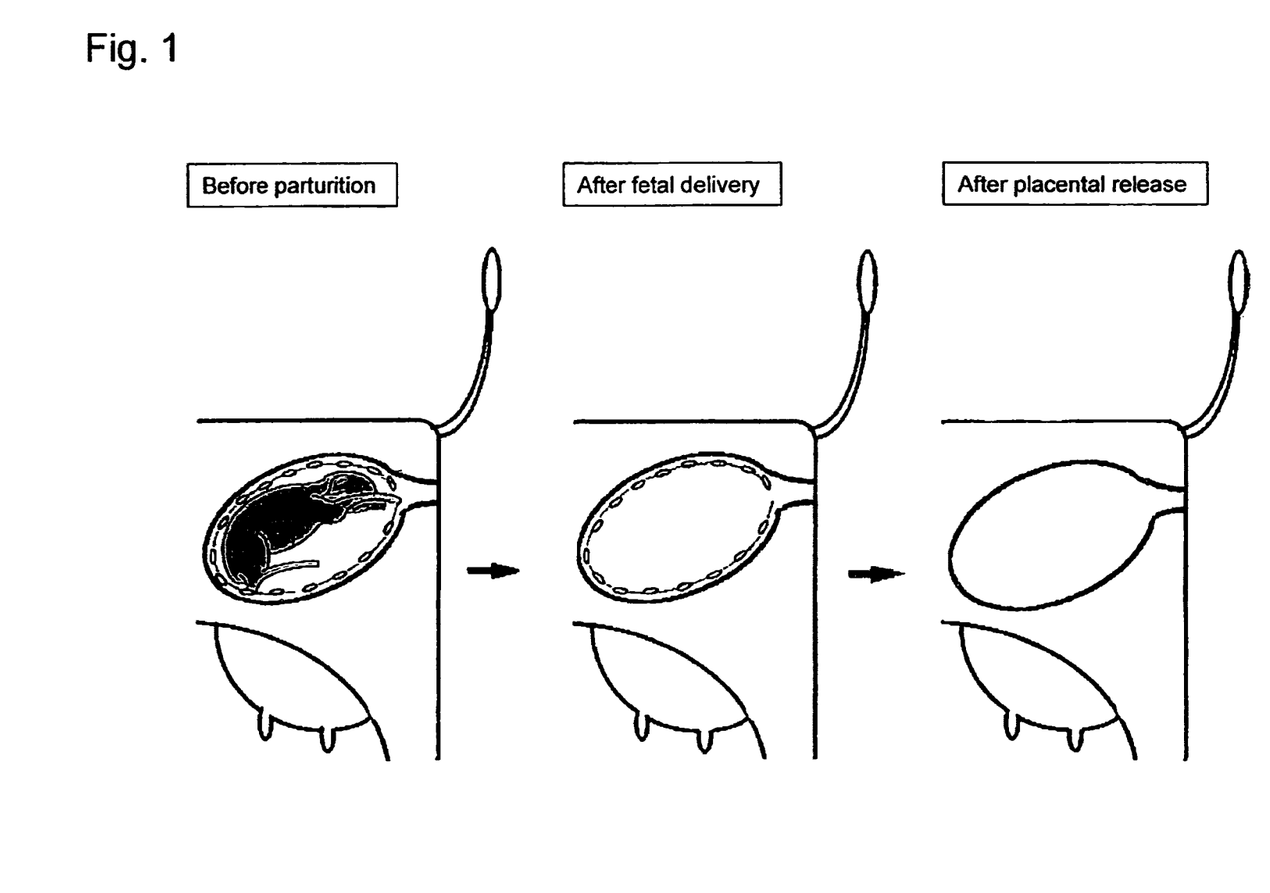
FIG. 1 is a schematic diagram showing the progress of parturition.

As shown in FIG. 1, the parturition is achieved in two stages of the fetal delivery and the placental release. In the abovementioned parturition induction using glucocorticoid or prostaglandin, the fetal delivery serving as the first stage of the parturition is induced. Glucocorticoid promotes the production of prostaglandin and prostaglandin has luteolytic and oxytocic actions. Because of these actions, the administration of glucocorticoid or prostaglandin induces the fetal delivery (Nakahara et al., Kachiku Hansyokushi (Journal of Veterinary Reproduction), Vol. 21, No. 4, p. 135-140 (1976); Uemura et al., Kachiku Hansyokushi (Journal of Veterinary Reproduction), Vol. 23, No. 3, p. 85-91 (1977); and Aihara et al., Kachiku Shinryo (Journal of Veterinary Clinic), Vol. 52, No. 11, p. 673-681 (2005)). In the concerned parturition induction, calving occurs within about 1.5 to 2 days post administration of glucocorticoid or prostaglandin, although the incidence of the placental retention is high. Accordingly, the concerned parturition induction has problems such as a pathologic condition in which the placenta is not released even though the fetus is delivered (retained afterbirth).

In this way, there has been no known safe and innovative technique for controlling the parturition yet.

BRIEF SUMMARY OF THE INVENTION

As described above, there has been no known innovative technique for controlling the parturition. On the other hand, it has been conventionally known that the fetal delivery serving as the first stage of the parturition is caused by the luteolysis and the uterine contraction triggered by prostaglandin. However, researches are not in progress regarding the release of unneeded placenta serving as the second stage, and the mechanism which induces the placental release has not been known yet.

Therefore, in view of the above situations, the inventor of the present invention has conducted studies on the mechanism which induces the placental release at the second stage of the parturition with an objective of identifying activators of the concerned mechanism and providing methods for placental exfoliation using these activators.

As a result of intensive studies to solve the above problems, the inventor of the present invention identified the association of matrix metalloprotease (hereunder, referred to as "MMP") as a mechanism which induces the placental release, and found out that activators of MMP are arachidonic acid (alternatively, referred to as "5,8,11,14-eicosatetraenoic acid") derivatives and the like. This has led to the completion of the present invention.

The present invention relates to a composition for placental exfoliation containing a compound selected from the group consisting of an arachidonic acid derivative, a linoleic acid, an α-linolenic acid, a γ-linolenic acid, a stearidonic acid, a dihomo-γ-linolenic acid, an ω-3-arachidonic acid, an eicosapentaenoic acid, a docosahexaenoic acid, and a salt thereof. The arachidonic acid derivative is exemplified by a 12-oxoarachidonic acid (alternatively, referred to as "12-oxoeicosatetraenoic acid") and metabolites thereof. Moreover, metabolites of the abovementioned highly unsaturated fatty acids (such as an eicosapentaenoic acid and a docosahexaenoic acid) may also be employed as active ingredients of the composition for placental exfoliation.

Moreover, the present invention relates to a kit for parturition induction comprising the abovementioned composition for placental exfoliation. The kit for parturition induction may comprise a composition for fetal delivery containing a glucocorticoid or prostaglandin.

Further, the present invention relates to a method for placental exfoliation comprising the step of administering a compound selected from the group consisting of an arachidonic acid derivative, a linoleic acid, an α-linolenic acid, a γ-linolenic acid, a stearidonic acid, a dihomo-γ-linolenic acid, an ω-3-arachidonic acid, an eicosapentaenoic acid, a docosahexaenoic acid, and a salt thereof, to a mammal after fetal delivery. The mammal is exemplified by a cow. The arachidonic acid derivative is exemplified by a 12-oxoarachidonic acid and metabolites thereof.

Moreover, the present invention relates to a method for parturition induction comprising the steps of: administering a glucocorticoid or prostaglandin to a mammal in the gestation period so as to induce fetal delivery; and administering a compound selected from the group consisting of an arachidonic acid derivative, a linoleic acid, an α-linolenic acid, a γ-linolenic acid, a stearidonic acid, a dihomo-γ-linolenic acid, an ω-3-arachidonic acid, an eicosapentaenoic acid, a docosahexaenoic acid, and a salt thereof, to the mammal after the fetal delivery, so as to induce placental release. The mammal is exemplified by a cow. The arachidonic acid derivative is exemplified by a 12-oxoarachidonic acid and metabolites thereof.

Further, the present invention relates to a composition for MMP activation containing a compound selected from the group consisting of an arachidonic acid derivative, a linoleic acid, an α-linolenic acid, a γ-linolenic acid, a stearidonic acid, a dihomo-γ-linolenic acid, an ω-3-arachidonic acid, an eicosapentaenoic acid, a docosahexaenoic acid, and a salt thereof. The arachidonic acid derivative is exemplified by a 12-oxoarachidonic acid and metabolites thereof.

Moreover, the present invention relates to a method for MMP activation comprising the step of administering a compound selected from the group consisting of an arachidonic acid derivative, a linoleic acid, an α-linolenic acid, a γ-linolenic acid, a stearidonic acid, a dihomo-γ-linolenic acid, an ω-3-arachidonic acid, an eicosapentaenoic acid, a docosahexaenoic acid, and a salt thereof, to a mammal. The mammal is exemplified by a cow. The arachidonic acid derivative is exemplified by a 12-oxoarachidonic acid and metabolites thereof.

According to the present invention, the placenta can be released without causing the placental retention. Moreover, according to the present invention, the parturition can be safely controlled.

This description includes part or all of the contents as disclosed in the description and/or drawings of Japanese Patent Application No. 2007-246032, which is a priority document of the present application.

BRIEF DESCRIPTION OF THE DRAWINGS

The patent or application file contains at least one drawing executed in color. Copies of this patent or patent application publication with color drawing(s) will be provided by the office upon request and payment of the necessary fee.

PREFERRED EMBODIMENTS OF THE INVENTION

Hereafter, the present invention will be described in detail.

The composition for placental exfoliation of the present invention contains a compound selected from the group consisting of an arachidonic acid derivative, a linoleic acid, an α-linolenic acid, a γ-linolenic acid, a stearidonic acid, a dihomo-γ-linolenic acid, an ω-3-arachidonic acid, an eicosapentaenoic acid, a docosahexaenoic acid, and a salt thereof (hereunder, may be referred to as the "active ingredient of the present invention" in some cases). The composition for placental exfoliation of the present invention allows the placenta to be exfoliated and released to the outside from the body of a mammal administered with the composition after the fetal delivery. Here, the term "placental exfoliation" refers to a phenomenon in which the maternal placenta and the fetal placenta are separated after the fetal delivery to release the unneeded fetal placenta out from the uterus. The subject to be administered with the composition for placental exfoliation of the present invention is exemplified by mammals such as human, cow, pig, horse, sheep, goat, monkey, dog, and cat, and particularly preferably cow.

In the present invention, the arachidonic acid derivative refers to a 12-lipoxygenase metabolite of an arachidonic acid. The 12-lipoxygenase is a redox enzyme which adds a molecular oxygen to an unsaturated fatty acid having a cis, cis-1,4-pentadiene structure so as to introduce a hydroperoxide group to a carbon at the position 12. Examples of the arachidonic acid derivative include a 12-oxoarachidonic acid and metabolites thereof, a 12(S)-hydroperoxyarachidonic acid (alternatively, referred to as "12(S)-hydroperoxyeicosatetraenoic acid"), a 12(R)-hydroperoxyarachidonic acid (alternatively, referred to as "12(R)-hydroperoxyeicosatetraenoic acid"), a 12(S)-hydroxyarachidonic acid (alternatively, referred to as "12(S)-hydroxyeicosatetraenoic acid"), and a 12(R)-hydroxyarachidonic acid (alternatively, referred to as "12(R)-hydroxyeicosatetraenoic acid"). In particular, a 12-oxoarachidonic acid and metabolites thereof are preferred.

The arachidonic acid derivative can be produced, for example, by a chemical synthesis, or by reacting an arachidonic acid with a 12-lipoxygenase (O'Flaharty, Biochim. Biophys. Acta, 1994, 1201:505-515). Alternatively, commercially available products may be employed for the arachidonic acid derivative.

Furthermore, the composition for placental exfoliation of the present invention may contain a further derivative of a 12-oxoarachidonic acid, a highly unsaturated fatty acid other than an arachidonic acid (such as an eicosapentaenoic acid, a docosahexaenoic acid, an α-linolenic acid, a stearidonic acid, and an ω-3-arachidonic acid) or a metabolite thereof, or a precursor of an arachidonic acid (such as a linoleic acid, a γ-linolenic acid, and a dihomo-γ-linolenic acid) as an active ingredient, instead of, or along with, the arachidonic acid derivative. These compounds have a placental exfoliation effect or an MMP activation effect similar to those of the arachidonic acid derivative. These compounds can be produced, for example, by a chemical synthesis, or by utilizing the extraction from plant bodies or fish oils, or the microbial fermentation (Osamu Suzuki et al., Kinosei Shishitsu No Shinten (Recent Development of Functional Lipids) (2006)). Alternatively, commercially available products may be employed for these compounds.

Examples of the salts of an arachidonic acid derivative, a linoleic acid, an α-linolenic acid, a γ-linolenic acid, a stearidonic acid, a dihomo-γ-linolenic acid, an ω-3-arachidonic acid, an eicosapentaenoic acid, and a docosahexaenoic acid include pharmaceutically acceptable salts. Such salts are exemplified by alkali metal salts such as sodium salts and potassium salts.

The composition for placental exfoliation of the present invention is preferably sterile and may contain one or more pharmaceutically acceptable carriers, excipients or diluents or other components. It may contain various optional components (such as an excipient, a binder, a disintegrator, a surfactant, a lubricant, a flow promoter, a diluent, a flavoring agent, a colorant, and a fragrant agent) for use of normal medicaments, veterinary medicaments, or the like, in addition to the active ingredient of the present invention.

Examples of the excipient include celluloses (such as crystalline cellulose), starches (such as rice starch, potato starch, corn starch, wheat starch, and a starch), dextrin, dextran, sugar alcohols (such as mannitol, erythritol, xylitol, maltose, maltitol, and sorbitol), lactose, and glucose.

Examples of the binder include starches, dextrins, powdered acacia, gelatin, hydroxypropyl starch, methylcellulose, carboxymethylcellulose sodium, hydroxypropylcellulose, crystalline cellulose, ethylcellulose, polyvinylpyrrolidone, and macrogol.

Examples of the disintegrator include starches, hydroxypropyl starch, carboxymethylcellulose sodium, carboxymethylcellulose calcium, carboxymethylcellulose, and low substituted hydroxypropylcellulose.

Examples of the surfactant include sodium lauryl sulfate, soybean lecithin, sucrose fatty acid esters, and polysorbate 80.

Examples of the lubricant include talc, waxes, hydrogenated vegetable oils, sucrose fatty acid esters, magnesium stearate, calcium stearate, aluminum stearate, and polyethylene glycol.

Examples of the flow promoter include light anhydrous silicic acid, dried aluminum hydroxide gel, synthetic aluminum silicate, and magnesium silicate.

Examples of the diluent include distilled water for injection, saline, glucose aqueous solution, olive oil, sesame oil, peanut oil, soybean oil, corn oil, propylene glycol, polyethylene glycol, and ethyl alcohol.

Moreover, the composition for placental exfoliation of the present invention may also contain further additional components.

The dosage form of the composition for placental exfoliation of the present invention is appropriately selected as required, examples of which include oral agents such as tablets, capsules, granules, fine granules, and powder, and parenteral agents such as injections and suppositories. The route of administration of the composition for placental exfoliation of the present invention is appropriately determined in accordance with the dosage form, examples of which include oral administrations and parenteral administrations (such as intravenous administration, intramuscular administration, subcutaneous administration, intrarectal administration, intranasal administration, and sublingual administration).

The frequency of administration, the dose of administration, and the timing of administration of the composition for placental exfoliation of the present invention are not particularly limited, but may be appropriately determined in accordance with, for example, the type, the age, and the body weight of the mammal, and the degree of the symptom. The frequency of administration is, for example in the administration by means of the intravenous injection, once to several times (such as twice, three times, four times, and five times) after the fetal delivery, and preferably once. The dose of administration of the composition for placental exfoliation of the present invention is, for example in cases of cows, 1 to 5 mg/subject per each time, and preferably 2.0 to 10.0 µg/kg of body weight per each time, in terms of the active ingredient of the present invention contained therein. Moreover, the timing of administration is, for example, within 12 hours or less after the fetal delivery, and preferably within 2 to 6 hours.

The pharmacological evaluation of the composition for placental exfoliation of the present invention may be carried out either in vitro or in vivo.

The in vitro pharmacological evaluation is exemplified by a method using cultured fibroblasts derived from the placenta (MMP-producing cells). First, the composition for placental exfoliation of the present invention is added to a culture medium of the concerned cultured fibroblasts. After the addition, the cells are cultured for a fixed period of time. Then, in cases where a significantly large number of these cells were separated from a solid phase (such as the bottom of the culture plate) as compared to the negative control (without the addition of the composition for placental exfoliation of the present invention, for example), the composition for placental exfoliation of the present invention can be judged as having the placental exfoliation effect.

The in vivo pharmacological evaluation is exemplified by a method using cows which have delivered fetuses by means of the single administration of a prostaglandin. First, the composition for placental exfoliation of the present invention is administered to cows after the fetal delivery. Next, after the administration, in cases where the placenta is released significantly earlier as compared to the negative control (without the administration of the composition for placental exfoliation of the present invention, for example), the composition for placental exfoliation of the present invention can be judged as having the placental exfoliation effect.

The composition for placental exfoliation of the present invention can also be provided as a safe kit for parturition induction (hereunder, referred to as the "kit for parturition induction of the present invention"). In particular, the kit for parturition induction of the present invention is achieved by combining the composition for placental exfoliation of the present invention with a composition for fetal delivery containing either glucocorticoid or prostaglandin. The use of such a kit for parturition induction of the present invention enables the induction of both two stages of the fetal delivery and the placental release in the parturition. In the kit for parturition induction of the present invention, the composition for placental exfoliation of the present invention and the composition for fetal delivery can be provided in the forms of being contained in separate containers or the like.

A kit may contain a sterile composition containing an amount of a glucocorticoid and/or prostaglandin sufficient to induce fetal delivery of a mammal and a sterile composition comprising a 12-oxoarachidonic acid or a metabolite thereof, or a salt thereof, sufficient to induce placental exfoliation, and optionally instructions explaining how to administer or use these compositions to facilitate fetal delivery and placental exfoliation. Kits may contain single or multiple dosages of one or both of these sterile compositions, wherein each dosage may be in a separate container, vial, or syringe. Preferably, each dose contains about 2.0 to 10.0 µg of 12-oxoarachidonic acid or a metabolite thereof, or a salt thereof per kg of body weight of said mammal. For example, where the average weight of a cow is about 500 kg, such a kit may contain 1 mg to 5 mg of 12-oxoarachidonic acid or a metabolite thereof, or a salt thereof or for or a human female whose average body weight is about 70 kg, a dosage of 140 µg to 700 µg may be used. These dosages are representative and one of skill in the art may select a higher or lower dosage based on the body weight of the mammal to be treated as well as other pharmaceutical or therapeutic considerations.

The glucocorticoid or prostaglandin is commercially available from veterinary pharmaceutical manufacturers (such as Pfizer Inc.).

The dosage form, the route of administration, the frequency of administration, and the dose of administration of the composition for fetal delivery may be in accordance with the above description regarding the composition for placental exfoliation of the present invention.

The timing of administration of the composition for fetal delivery is exemplified by gestation periods from 10 days before the due date to cases of beyond the due date, and preferably a week before the due date, but is not to be limited thereto. That is to say, the administration of the composition for fetal delivery is conducted prior to the administration of the composition for placental exfoliation of the present invention.

Meanwhile, the method for placental exfoliation of the present invention comprises the step of administering an active ingredient of the present invention to a mammal after the fetal delivery. Moreover, the method for parturition induction of the present invention comprises the step of administering a glucocorticoid or prostaglandin to a mammal in the gestation period, and the step of administering an active ingredient of the present invention to the mammal after the fetal delivery. Hereunder, the method for placental exfoliation of the present invention and the method for parturition induction of the present invention are collectively referred to as the "method of the present invention".

The mammal in the method of the present invention is exemplified by mammals such as human, cow, pig, horse, sheep, goat, monkey, dog, and cat, and particularly preferably cow.

In the method of the present invention, the route of administration, the frequency of administration, the dose of administration, and the timing of administration of the active ingredient of the present invention, or a glucocorticoid or prostaglandin may be in accordance with the above descriptions regarding the composition for placental exfoliation and the kit for parturition induction of the present invention.

According to the present invention described above, the parturition can be induced at a desired timing (for example, daytime) without causing placental retention. Moreover, according to the present invention, even in cases where the parturition would not occur beyond the due date and the fetus grows so oversized that the difficult delivery is predicted, the parturition can be promptly induced without causing placental retention. Furthermore, according to the present invention, the uterus is expected to be recovered at an early stage, which is considered to lead to the improvement of the reproductive performance. Moreover, the present invention is not only applicable to the control of the date and time of parturition, but is also applicable to the treatment for the naturally-occurring placental retention.

Meanwhile, the composition for MMP activation of the present invention contains the abovementioned active ingredient of the present invention. Moreover, the method for MMP activation of the present invention is a method comprising the step of administering the abovementioned active ingredient of the present invention to a mammal. According to the composition for MMP activation of the present invention or the method for MMP activation of the present invention, a subject requiring the MMP activation (for example, a patient suffering from a disease such as residual placenta) can be treated.

Here, the MMP activation refers to a phenomenon in which a peptide of an MMP precursor enzyme (also, referred to as a proenzyme, which is an inactive state) is partially cleaved to express its activity (such as a collagen degrading activity). The MMP to be activated is exemplified by MMP-2, MMP-9, and the like.

The composition for MMP activation of the present invention can be produced and used in accordance with the above descriptions regarding the composition for placental exfoliation of the present invention. Moreover, the method for MMP activation of the present invention can be carried out in accordance with the above descriptions regarding the method of the present invention. The frequency of administration, the timing of administration, and the period of administration thereof may be appropriately determined in accordance with, for example, the type, the age, and the body weight of the mammal, and the degree of the symptom.

The pharmacological evaluation of the composition for MMP activation of the present invention is exemplified by the abovementioned in vitro method using cultured fibroblasts derived from the placenta (MMP-producing cells), or a method using gelatin zymography.

In the method using gelatin zymography, first, the composition for MMP activation of the present invention is brought into contact with MMP-producing cells. After the incubation for a fixed time, the cells are lysed to make a protein solution, which is then subjected to an electrophoresis using a SDS polyacrylamide electrophoresis gel containing a gelatin (MMP substrate). After the migration, the temperature was kept for a fixed time to progress the enzyme reaction, followed by staining of undegraded gelatin remaining in the gel. In cases where a significantly greater amount of the gelatin was degraded as compared to the negative control (without the contact with the composition for MMP activation of the present invention, for example), the composition for MMP activation of the present invention can be judged as having the MMP activation effect.

EXAMPLES

The present invention is hereafter described in greater detail with reference to the following examples, although the technical scope of the present invention is not limited thereto.

Example 1

Placental Exfoliation by the Administration of 12-oxoarachidonic acid (1) Search for MMP Activators The main cause of failure in the placental release during the parturition is failure in the normal separation (exfoliation) between the maternal placenta and the fetal placenta. There are reports showing that the placenta of cows suffering from placental retention has low or no detected activity of a certain type of MMP, and that the injection of a collagenase through the umbilical cord into cows suffering from placental retention facilitates the placental exfoliation (MMP is also a collagenase), thus it can be assumed that MMP is associated with the placental exfoliation (Maj et al., Placenta, 1997, 18:683-687; Eiler et al., JAVMA, 1993, 203:436-443). The concerned MMP widely exists as a precursor enzyme (proenzyme) in vivo, and the enzyme has to be activated to exert its functions.

Therefore, cultured fibroblasts derived from the placenta (MMP-producing cells) were used to search for MMP activators.

1-1. Candidate Compounds for MMP Activators

Commercially available products were employed for the candidate compounds for MMP activators in all cases.

1-2. Search for MMP Activators

Since in vivo MMP-2 is produced from fibroblasts, fibroblasts were prepared from bovine fetal placenta. A fixed amount of cells were seeded on the culture plate, and were treated with cortisol after the monolayer formation. Further, the MMP activator candidate compounds were added thereto. If an MMP activator candidate compound had an MMP activation ability, cells were exfoliated from the culture plate and floated therein.

Figure 2:
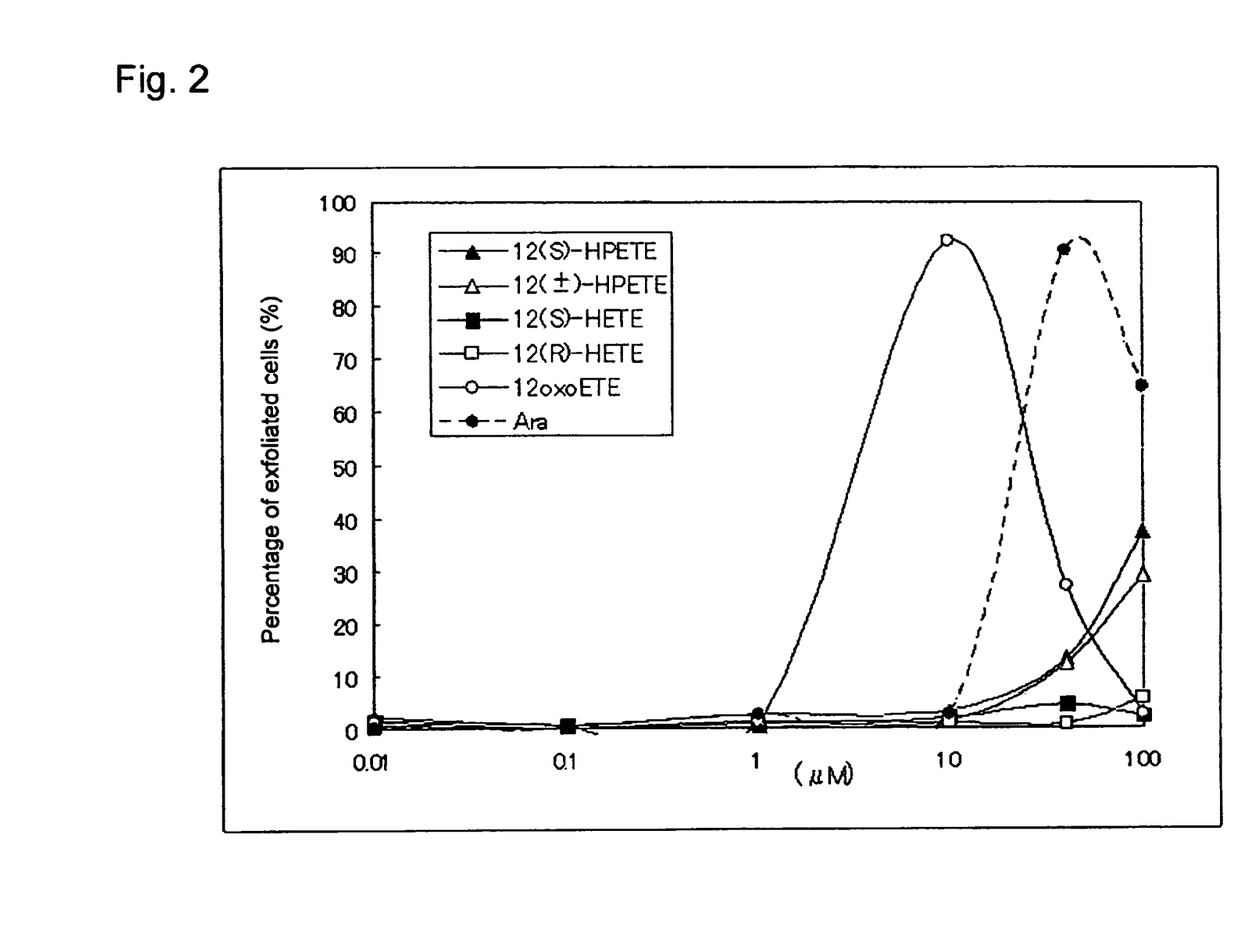
FIG. 2 is a characteristic chart showing the cell exfoliation activity of arachidonic acid derivatives.
Figure 3:
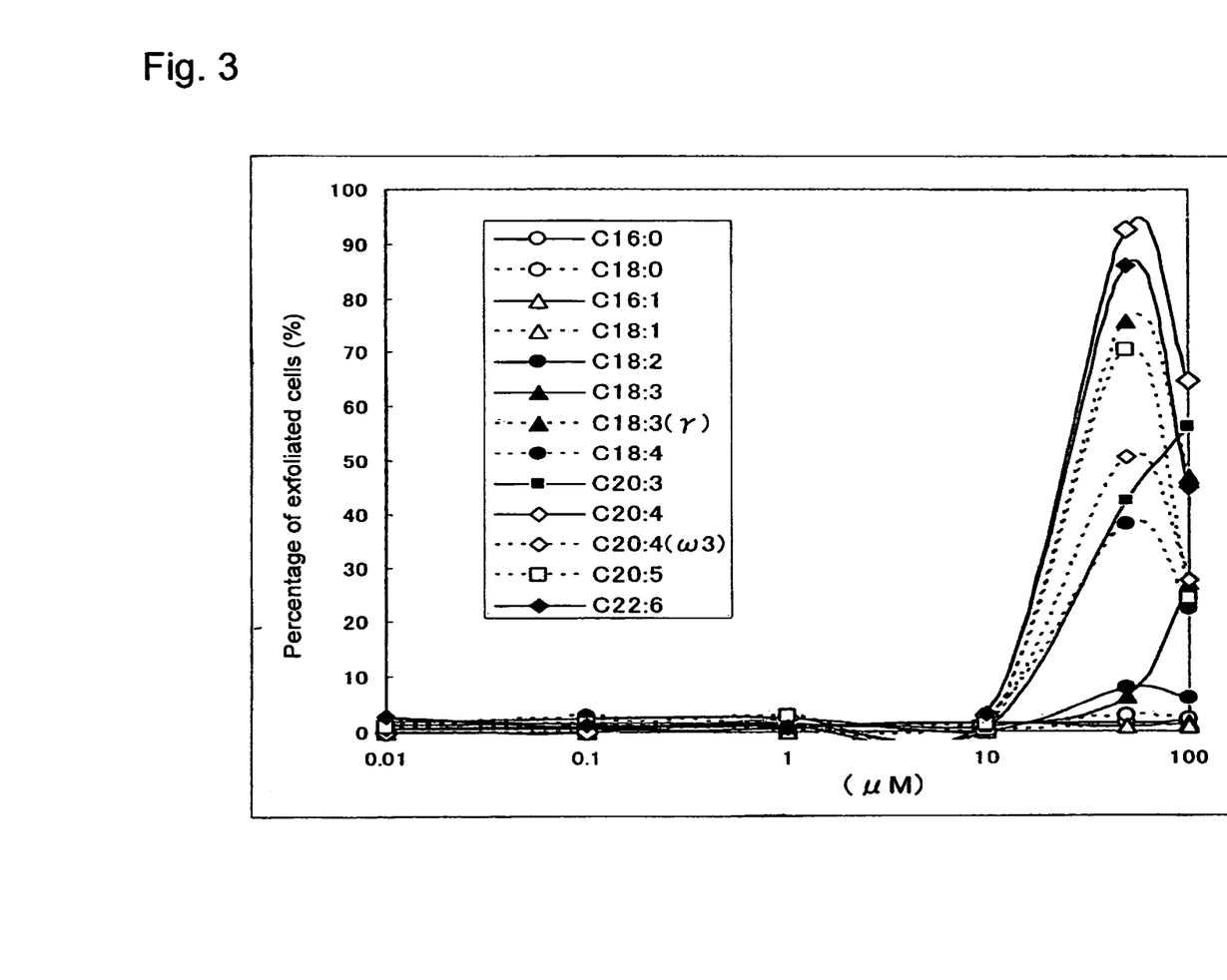
FIG. 3 is a characteristic chart showing the cell exfoliation activity of highly unsaturated fatty acids.

The results are shown in FIG. 2 and FIG. 3. In FIG. 2 and FIG. 3, the y-axis shows the percentage of exfoliated cells (%)

relative to the non-treatment (0%) while the x-axis shows the concentration (μM) of the added compound.

The meanings of the abbreviations in FIG. 2 are as follows.
"12(S)-HPETE": 12(S)-hydroperoxyarachidonic acid
"12(±)-HPETE": 12(±)-hydroperoxyarachidonic acid (mixture of 12(S)-hydroperoxyarachidonic acid and 12(R)-hydroperoxyarachidonic acid)
"12(S)-HETE": 12(S)-hydroxyarachidonic acid
"12(R)-HETE": 12(R)-hydroxyarachidonic acid
"12oxoETE": 12-oxoarachidonic acid
"Ara": arachidonic acid Meanwhile, the meanings of the abbreviations in FIG. 3 are as follows.
"C16:0": palmitic acid
"C18:0": stearic acid
"C16:1": palmitoleic acid
"C18:1": oleic acid
"C18:2": linoleic acid
"C18:3": α-linolenic acid
"C18:3(γ)": γ-linolenic acid
"C18:4": stearidonic acid
"C20:3": dihomo-γ-linolenic acid
"C20:4": arachidonic acid
"C20:4(ω3)": ω-3-arachidonic acid
"C20:5": eicosapentaenoic acid
"C22:6": docosahexaenoic acid The signal transductions for the parturition that have been known so far are centrally mediated by cyclooxygenase derivatives of an arachidonic acid (prostanoid), and thus the first examination was performed in view of the possibility of MMP activation using the arachidonic acid. As shown in FIG. 2 and FIG. 3, the arachidonic acid (Ara) was confirmed to have a cell exfoliation activity (MMP activation ability). On the other hand, prostaglandin serving as cyclooxygenase derivatives of arachidonic acid had no cell exfoliation activity.

Three types of lipoxygenase pathways are known as other metabolic systems of arachidonic acid. Therefore, next, respective lipoxygenase inhibitors were jointly used to examine the reaction, which showed that a 12-lipoxygenase inhibitor inhibited the arachidonic acid-induced cell exfoliation. In this way, it was shown that the arachidonic acid was converted by a 12-lipoxygenase to exert its effect. Thus, cell exfoliation experiments were subsequently performed using 12-lipoxygenase derivatives (metabolites) of arachidonic acid.

As a result, as shown in FIG. 2, hydroxyderivatives of arachidonic acid (12(S)-hydroxyarachidonic acid (12(S)-HETE) and 12(R)-hydroxyarachidonic acid (12(R)-HETE)) had no cell exfoliation activities, while hydroperoxyderivatives of arachidonic acid (12(S)-hydroperoxyarachidonic acid (12(S)-HPETE) and 12(±)-hydroperoxyarachidonic acid (12(±)-HPETE)) showed weak cell exfoliation activities. Conversely, 12-oxoarachidonic acid (12oxoETE) serving as a ketone derivative of arachidonic acid showed a cell exfoliation activity at a lower concentration than that of the arachidonic acid itself (FIG. 2). That is to say, it was understood that the 12-oxoarachidonic acid had a stronger MMP activation ability.

On the other hand, as shown in FIG. 3, some highly unsaturated fatty acids, which belong to the same category as that of the arachidonic acid, showed cell exfoliation activities (medium activity: γ-linolenic acid, eicosapentaenoic acid, and docosahexaenoic acid, and weak activity: linoleic acid, α-linolenic acid, stearidonic acid, dihomo-γ-linolenic acid, and ω-3-arachidonic acid), all of which were however weaker than the activity of 12-oxoarachidonic acid. However, further metabolites of these highly unsaturated fatty acids and 12-oxoarachidonic acid might be found to have stronger cell exfoliation activities. These substances can also be used for promoting the placental exfoliation.

(2) Placental exfoliation by the administration of 12-oxoarachidonic acid

In order to induce the fetal delivery, a formulation (10 ml) containing a naturally-occurring prostaglandin (50 mg) was intramuscularly injected into the hip of a pregnant Holstein cow (dairy cow) (body weight 779 kg) a week prior to the due date. Moreover, a cow after the third calving was again administered with the prostaglandin after 12 hours from the first injection thereof (evening on the first day).

In the morning on the third day from the administration of prostaglandin, the pregnant cow delivered a fetus. The mother cow and the newborn calf were both healthy.

Figure 4:
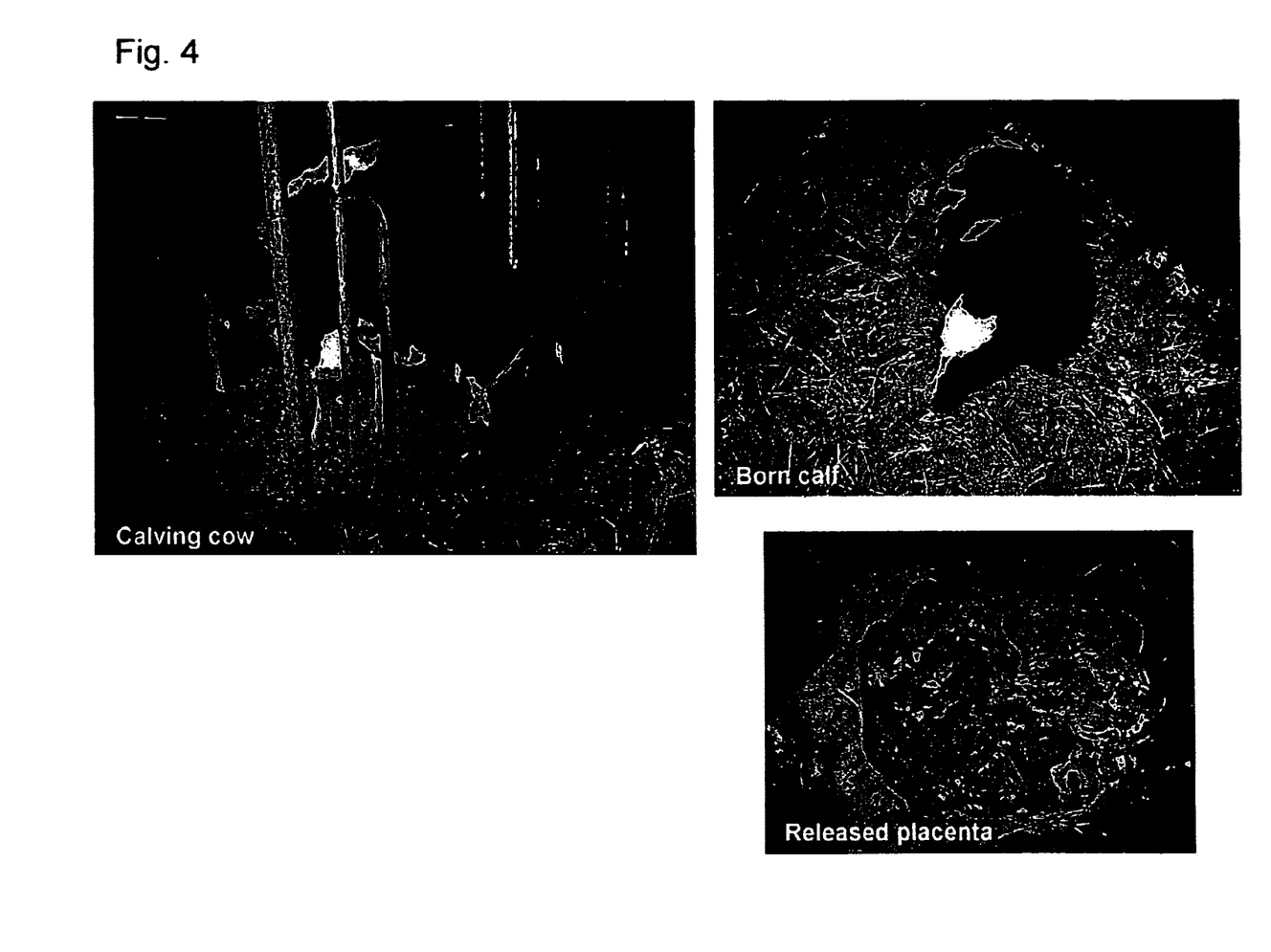
FIG. 4 presents photographs showing the success of placenta release by 12-oxoarachidonic acid.

Next, after 4 hours from the fetal delivery, a saline solution (15 ml) containing 12-oxoarachidonic acid (1 mg) was intrajugularly injected into the mother cow which had delivered a fetus. After about 6 hours from the injection, the whole amount of the placenta was released from the mother cow. FIG. 4 presents photographs showing the manner of such parturition. The postexperimental mother cow got pregnant again, showing that the reproductive function was not affected. In cases of the non-administration of 12-oxoarachidonic acid, the placenta was not released from the mother cow, and the placental retention occurred.

(3) MMP Activity in Released Placenta

The MMP activity in released placenta was analyzed. The samples were as follows: a placenta released from a mother cow of normal parturition (without specific treatment) (expressed as "normal parturition" in FIG. 5); a placenta from a mother cow which was subjected to the fetal delivery induction with a prostaglandin but suffered from placental retention (expressed as "PG-induced parturition" in FIG. 5); a placenta released from a mother cow which was subjected to the fetal delivery induction with a prostaglandin and the subsequent placental release induction with a 12-oxoarachidonic acid (expressed as "PG-induction+oxo" in FIG. 5); and a placenta from a mother cow which had naturally-occurring placental retention (expressed as "placental retention cow" in FIG. 5).

The MMP activity was measured using gelatin zymography. That is to say, a gelatin serving as an MMP substrate was previously contained in a normal SDS polyacrylamide electrophoresis gel. The placenta samples were subjected to electrophoresis using the gel, and then SDS was removed therefrom. The temperature of the gel was kept with a buffer, and thereby MMP active portions in the gelatin were degraded in accordance with the strength of the activity. After the reaction, the gel was subjected to the protein staining, by which the MMP active portions in the gel remained unstained and thus were detected as white bands. The activity was detected only for the proenzyme. Therefore, in cases of success in the MMP activation, the band of the proenzyme activity would be observed weak in the gel. Conversely, in cases of failure in the MMP activation, the proenzyme is accumulated, making the band strong. The proenzyme is autoactivated within the gel, and thus is detectable as the activity. The results are shown in FIG. 5.

Figure 5:
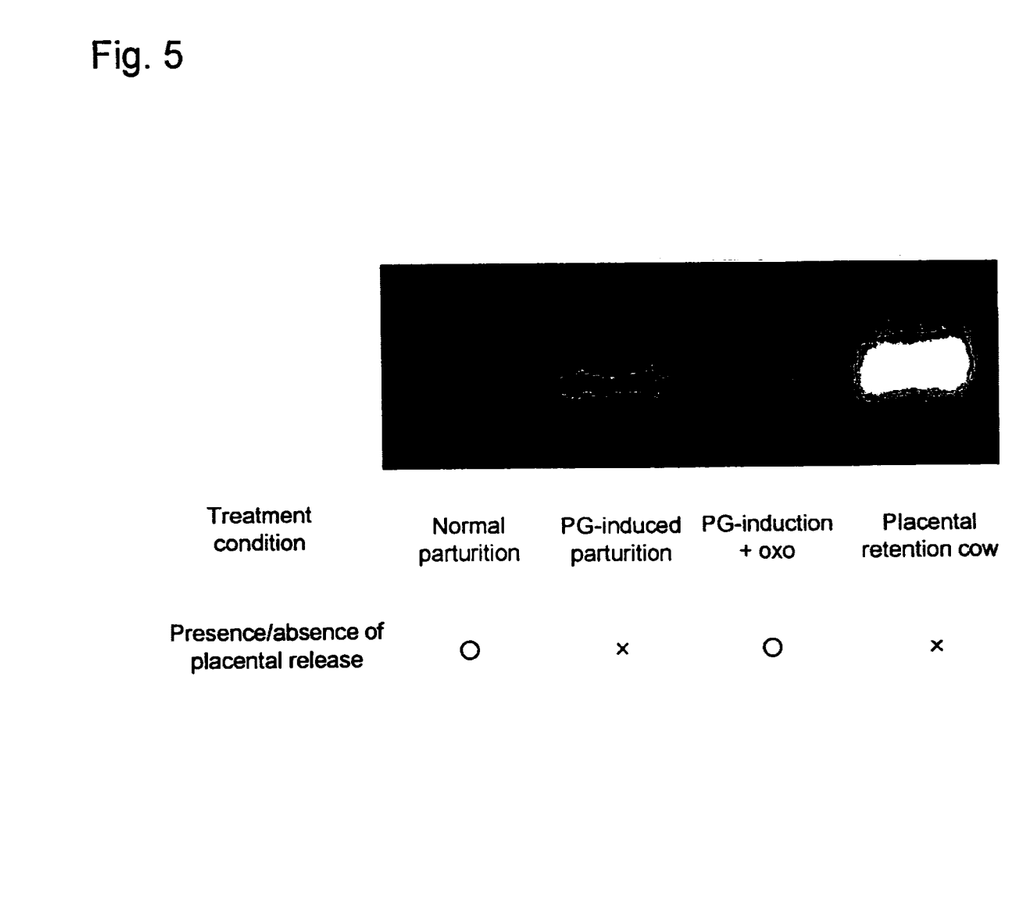
FIG. 5 presents a photograph showing the proMMP activity in released or attached placentas.

As shown in FIG. 5, the placenta released from the mother cow subjected to the fetal delivery induction with a prostaglandin and the subsequent placental release induction with a 12-oxoarachidonic acid showed an MMP pattern very close to that of the placenta released from the cow of normal parturition, which was apparently different from those of the placentas from the cow having naturally-occurring placental retention and the cow having prostaglandin-induced placental retention.

This fact is considered to be the evidence proving that the administration of 12-oxoarachidonic acid activated MMP to induce the placental exfoliation.

All publications, patents, and patent applications cited herein are incorporated herein by reference in their entirety.

The invention claimed is:

1. A kit for inducing fetal delivery and placental exfoliation in a cattle comprising:
   (i) a sterile composition containing an amount of a glucocorticoid and/or prostaglandin sufficient to induce fetal delivery of cattle; and
   (ii) a sterile composition containing an amount of 12-oxoarachidonic acid or a salt thereof, sufficient to induce placental release or placental exfoliation in cattle,
   separate containers for (i) and (ii), wherein for (i) said container sterilely holds an amount of glucocorticoid and/or prostaglandin sufficient to induce partrition in a cattle, and wherein for (ii) said container sterilely holds an amount of 12-oxoarchionic acid sufficient to induce placental release or placental exfoliation in a cattle; and
   instructions explaining how to administer the glucocorticoid and/or prostaglandin to induce partrition and or use these compositions to facilitate fetal delivery and how to administer the 12-oxoarachindonic acid to induce placental release or placental exfoliation in cattle.

2. The kit of claim 1 that comprises (ii) a sterile composition containing an amount of 12-oxoarachidonic acid or a salt thereof, sufficient to induce placental release or exfoliation in a cow.

3. The kit of claim 2 that comprises (ii) a sterile composition containing 1 mg to 5 mg of 12-oxoarachidonic acid or a salt thereof.

4. The kit of claim 1 that contains multiple doses of (i) and/or (ii) in separate containers.

5. The kit of claim 1, wherein the separate containers are at least one selected from the group consisting of a vial or syringe.

6. The kit of claim 1 that contains instructions explaining how to administer or use (i) and (ii) to facilitate fetal delivery and placental exfoliation in cattle; wherein (i) contains a dose of glucocorticoid and/or prostaglandin sufficient to induce fetal delivery in said cattle, and (ii) contains about 2.0 to 10.0 µg of 12-oxoarachidonic acid or a salt thereof per kg of body weight of said cattle.

7. The kit of claim 1 that comprises:
   (i) a sterile composition containing an amount of prostaglandin sufficient to induce fetal delivery of cattle; and
   (ii) a sterile composition containing an amount of 12-oxoarachidonic acid sufficient to induce placental exfoliation, and
   separate vials for (i) and (ii).

8. The kit of claim 1 that comprises:
   (i) a sterile composition containing an amount of prostaglandin sufficient to induce fetal delivery of cattle; and
   (ii) a sterile composition containing an amount of 12-oxoarachidonic acid sufficient to induce placental exfoliation, and
   separate syringes for (i) and (ii).

* * * * *

UNITED STATES PATENT AND TRADEMARK OFFICE
CERTIFICATE OF CORRECTION

| | |
|---|---|
| PATENT NO. | : 8,431,548 B2 |
| APPLICATION NO. | : 13/219364 |
| DATED | : April 30, 2013 |
| INVENTOR(S) | : Hachiro Kamada |

It is certified that error appears in the above-identified patent and that said Letters Patent is hereby corrected as shown below:

In the Claims:

Column 11, line 20, claim 1, "partrition" should read --parturition--;

22, "12-oxoarchionic acid" should read --12-oxoarachidonic acid--;

25, "partrition and or use" should read --parturition and/or use--;

27, "12-oxoarachindonic acid" should read --12-oxoarachidonic acid--;

Page 1 of 1

Signed and Sealed this
Third Day of September, 2013

Teresa Stanek Rea
*Acting Director of the United States Patent and Trademark Office*